United States Patent [19]

Yamazaki et al.

[11] Patent Number: 5,156,152
[45] Date of Patent: Oct. 20, 1992

[54] ULTRASONIC DIAGNOSING APPARATUS

[75] Inventors: Yoshiro Yamazaki; Shiuichi Kawasaki, both of Tochigi, Japan

[73] Assignee: Kabushiki Kaisha Toshiba, Kawasaki, Japan

[21] Appl. No.: 548,664

[22] Filed: Jul. 5, 1990

[30] Foreign Application Priority Data

Jul. 6, 1989 [JP] Japan .................................. 1-174434

[51] Int. Cl.⁵ .............................................. A61B 8/06
[52] U.S. Cl. ........................... 128/661.08; 128/661.09; 128/660.04; 128/662.02
[58] Field of Search ....................... 128/660.04, 660.05, 128/660.07, 660.08, 661.01, 661.07, 661.08, 661.09, 662.02

[56] References Cited

U.S. PATENT DOCUMENTS

| | | | |
|---|---|---|---|
| 4,230,124 | 10/1980 | Pickering et al. | 128/660.07 |
| 4,463,763 | 8/1984 | Koyano et al. | 128/660.04 |
| 4,690,150 | 9/1987 | Mayo, Jr. | 128/660.04 |
| 4,768,515 | 9/1988 | Namekawa | 128/661.09 |
| 4,817,619 | 4/1989 | Sugiyama et al. | 128/661.09 |
| 4,827,942 | 5/1989 | Lipschutz | 128/661.08 |
| 4,930,514 | 6/1990 | Baba et al. | 128/661.09 |

FOREIGN PATENT DOCUMENTS 0100094 2/1984 European Pat. Off. .
85/02105 5/1985 PCT Int'l Appl. .

OTHER PUBLICATIONS

Toshiba Review, No. 158, 1986, Tokyo, Japan, pp. 20–24, Seo et al., "An Ultrasound Blood Flow Imaging System, SSH-65A".

Primary Examiner—Francis Jaworski
Assistant Examiner—George Manuel
Attorney, Agent, or Firm—Cushman, Darby & Cushman

[57] ABSTRACT

An ultrasonic diagnosing apparatus displaying blood flow data. A Doppler shift signal is detected from a reception signal obtained by an ultrasonic transducer by transmitting/receiving an ultrasonic wave to/from an object. Doppler data obtained from this detection signal is written in a memory. Monochromatic ultrasonic image data and the Doppler data are used to perform color processing of the ultrasonic image data in accordance with the Doppler data. The apparatus includes a mixing/processing section and a switching control section. The mixing/processing section includes a reversing section for reversing display colors associated with moving directions by performing complement processing of the Doppler data read out from the memory, and a selector section for selecting one of the reversed and the non-reversed Doppler data. The mixing/processing section mixes the selected Doppler data with the ultrasonic image data. The switching control section serves to arbitrarily control a selecting operation of the selector section.

21 Claims, 4 Drawing Sheets

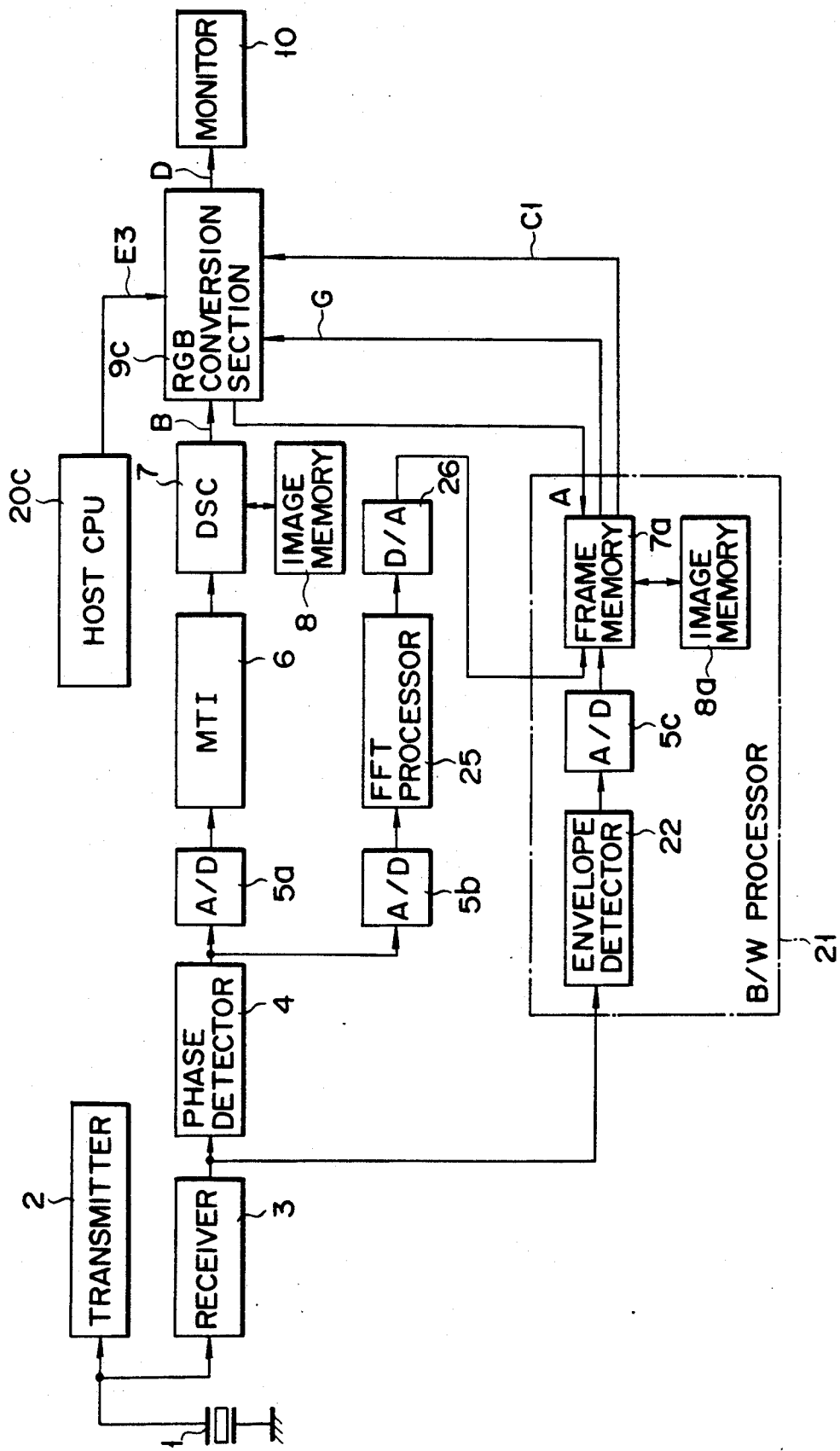
F I G. 5

ULTRASONIC DIAGNOSING APPARATUS

BACKGROUND OF THE INVENTION

1. Field of the Invention

The present invention relates to an ultrasonic diagnosing apparatus having a function of visually displaying function information associated with the movement of tissues of a living body, such as blood flow data, by an ultrasonic Doppler method of obtaining movement data of an object by using the Doppler effect of an ultrasonic wave.

2. Description of the Related Art

In ultrasonic diagnosing, diagnosis is performed on the basis of various information obtained by using an ultrasonic wave, e.g., anatomical information, typically a B-mode image, motion information of an organ of a living body, typically an M-mode image, and function information associated with the movement of tissues of a living body, which is obtained by using the Doppler effect, typically blood flow imaging.

When the above-described ultrasonic diagnosis is to be performed, a living body is scanned with an ultrasonic beam either by an electronic scanning method or by a mechanical scanning method. In the electronic scanning method, an ultrasonic beam is scanned by electronically controlling the drive timings of a plurality of transducer elements and/or the processing timings of echo signals received by a plurality of transducer elements. In the mechanical scanning method, an ultrasonic beam is scanned by mechanically moving an ultrasonic transducer. Electronic scanning will be described in detail below.

Electronic scanning is normally performed by using an ultrasonic transducer array in which a plurality of ultrasonic transducer elements are properly arranged.

In linear electronic scanning, a predetermined number of transducer elements of the above-mentioned transducer elements are used as a group, and one transmission/reception operation of an ultrasonic beam is performed by using this group. In this method, transducer elements selected as the group are sequentially switched to slide the transmission/reception position of an ultrasonic wave. For example, the transmission/reception position of an ultrasonic wave is electrically shifted by sequentially shifting/selecting transducer elements of the group one by one. In addition, the excitation timings and/or reception signal timings of elements of the selected transducer elements, which are respectively located at central and peripheral portions of the beam, are shifted from each other so as to focus the ultrasonic wave by using a difference in phase between sound waves generated by the respective transducer elements or the reception signals. This operation is called electronic focusing. An ultrasonic wave received by ultrasonic transducer elements, i.e., an ultrasonic wave reflected by tissues of a living body (ultrasonic echo), is subjected to predetermined processing as an electrical signal, and an image based on ultrasonic echo data, e.g., a tomographic image, is formed to be displayed on a TV (television) monitor or the like.

When sector electronic scanning is to be performed, the above-mentioned plurality of ultrasonic transducer elements are used as a group as a whole, the excitation timings and/or reception signal timings of the respective transducer elements are sequentially changed to sequentially steer an ultrasonic beam to be transmitted/received and to scan a sector-like region. The subsequent signal processing is basically the same as that in the above-described linear electronic scanning.

In addition to the above-described linear and sector electronic scanning methods, a combination or modification of these methods is employed to perform electronic scanning.

In the mechanical scanning method, an ultrasonic transducer is attached to a scanning mechanism, and the ultrasonic transducer is mechanically driven by the scanning mechanism so a to scan an ultrasonic beam.

B- and M-mode methods are typical ultrasonic imaging methods used for diagnosis. The B-mode method is used to obtain a B-mode image as a tomographic image by mixing signals obtained by transmission/reception of an ultrasonic wave. The M-mode method is used to obtain an M-mode image associated with changes in echo data over time, which is obtained by stationary scanning in the same beam direction. An M-mode image represents changes in position of an ultrasonic wave reflecting portion over time, and is suitably used to diagnose a moving organ such as a heart.

An ultrasonic Doppler method, typically blood flow imaging, is employed to visualize function information of a living body by obtaining data based on the movement of moving tissues in the living body. This method will be described in detail below.

In the ultrasonic Doppler method, movement data of a moving object is obtained by using the ultrasonic Doppler effect in which when an ultrasonic wave is reflected by the moving object, the frequency of the reflected wave is shifted in accordance with the moving velocity of the object. More specifically, an ultrasonic pulse having a predetermined frequency is transmitted into a living body, and a frequency shift based on the Doppler effect is obtained from changes in phase of the reflected wave (echo), thus obtaining data associated with the movement of the moving object as a reflection source of the echo.

According to the ultrasonic Doppler method, the directions of blood flows at various positions in a living body can be determined together with the states of the blood flows, e.g., whether the blood flows are disturbed or normal.

A conventional ultrasonic diagnosing apparatus capable of performing blood flow imaging based on the above-described ultrasonic Doppler method and normal B- and M-mode imaging will be described below with reference to FIG. 1.

In order to obtain blood flow data from an ultrasonic echo, an ultrasonic transducer 1 of, e.g., an array type is driven by a transmitter 2 so as to repeatedly transmit an ultrasonic pulse at a predetermined pulse rate frequency by a predetermined number of times in a given direction (beam direction). The ultrasonic wave is reflected by scattering tissues moving in a living body, blood cells in this case, and returns as an ultrasonic echo which underwent a Doppler shift (fr+$\Delta$fr). This ultrasonic echo is received by a receiver 3 through the ultrasonic transducer 1, and is phase-detected by a phase detector 4, thereby obtaining a signal consisting of phase data of only $\Delta$fr, i.e., a Doppler signal and a clutter component as an unnecessary low-frequency component. This signal is converted into a digital signal by an A/D (analog-to-digital) converter 5. The clutter component is then removed by an MTI filter constituted by a digital filter in an MTI 6 for performing MTI (moving target indicator) processing. In the MTI 6, a Doppler shift signal based on a blood flow is frequency-analyzed by a high-speed frequency analyzer, which employs an autocorrelation system for obtaining a color Doppler image in a real-time manner. As a result, Doppler data is obtained which includes moving direction (blood flow direction) data, moving velocity (blood flow velocity) data, velocity turbulence data, and Doppler signal power data. The Doppler data is written in a frame memory of a digital scan converter (DSC) 7. An image memory 8 stores data of a plurality of frames, as needed, and is used to perform cinematographic loop reproduction, in which these data are sequentially and repeatedly read out to be reproduced and displayed.

The Doppler data such as the power, turbulence, and velocity data read out from the frame memory of the DSC 7 are input to an RGB conversion section 9a in synchronicity with a horizontal sync signal from a display system (H synchronization).

The Doppler data are then converted into R (red), G (green), and B (blue) signals by the RGB conversion section 9a in response to a control signal El from a host CPU (central processing unit) 20a. As shown in FIG. 2, the RGB conversion section 9a comprises a color bar generator 11, multiplexers 12a and 12b, and an RGB conversion circuit 13. Doppler data B input from the DSC 7 to the RGB conversion section 9a is mixed with color bar data from the color bar generator 11 by the multiplexer 12a. This composite data is further mixed with B-mode data C from a B/W (black and white) processor 21 in synchronicity with the time phase thereof. The color bar data is data for displaying a color bar on the screen of a display 10 as a reference scale of color display. The B- or M-mode data C from the B/W processor 21 is image data consisting of an envelope-detected echo signal for displaying a B- or M-mode image on the screen of the display 10. In this case, scanning of an ultrasonic wave for the B or M mode including transmission/reception of the ultrasonic wave for the above-described Doppler method is performed, and the B/W processor 21 forms a B- or M-mode image from a signal obtained by performing envelope detection of a reception echo signal obtained by the receiver 3, and outputs it as black/white (B/W) image data C. Because it is apparent that the B/W processor 21 also includes a DSC and a cinematographic loop reproduction image memory, though they are not shown.

The data output from the multiplexer 12b is converted into an RGB signal D by the RGB conversion circuit 13 and is supplied to the monitor display 10.

In this manner, the color data based on the Doppler data such as the blood flow and velocity data is mixed with the B/W data for a B- or M-mode image, which is obtained by another system, by using the RGB conversion circuit 13. As a result, the composite data is displayed on the monitor 10 as, e.g., a two-dimensional blood flow velocity image, which is obtained by superposing the above-mentioned Doppler data on the B/W image such as the B- or M-mode image.

In the above-described conventional ultrasonic diagnosing apparatus, a Doppler shift component is uniquely converted into a color data signal in such a manner that a Doppler shift caused by the movement of the object in a direction to approach the ultrasonic transducer 1 is displayed in red, and a Doppler shift caused by the movement of the object in a direction to move away from the ultrasonic transducer 1 is displayed in blue.

In anatomy and the like, arteries and veins are normally indicated by red and blue, respectively. If the display colors of Doppler shifts coincide with this coloring, no problems are posed. However, if the display colors of Doppler shifts differ from the general display colors some confusion may be caused.

For example, when a carotid artery is to be clinically diagnosed, a Doppler signal effectively used for diagnosis is sometimes obtained only when the ultrasonic transducer is brought into contact with a neck portion of a patient so as to direct it to a head portion. In this case, since the display colors of Doppler shift components are uniquely determined, arteries and veins are respectively displayed in blue and red, contrary to the general classification by color. In such a case, an operator, e.g., a doctor, who is familiar with the general display colors, i.e., red representing arteries and blue representing veins, may confuse arteries with veins.

SUMMARY OF THE INVENTION

In order to solve the above-described problem, display colors may be reversed by, e.g., interchanging sin and cos signals upon quadrature detection by the phase detector 4.

In this method, however, an operator must always pay attention to proper blood flow directions from the moment, when the transducer 1 is brought into contact with a patient. This increases the operation load. In addition, forward/reverse direction display by display colors cannot be changed after a display image is frozen (generally, a write operation with respect to a DSC is inhibited).

According to another method, display color conversion can always be performed by arranging a conversion circuit for reversing display colors at the output stage of the RGB conversion section 9a. This reduces the operation load of an operator. However, this requires a very complicated conversion circuit, thus increasing the cost of the diagnosing apparatus.

It is, therefore, an object of the present invention to provide an ultrasonic diagnosing apparatus which allows an operator to arbitrarily reverse display colors i accordance with his/her request without paying too much attention to blood flow directions, to easily obtain accurate ultrasonic diagnosis information, and to reduce the operation load of the operator with a simple arrangement.

In an ultrasonic diagnosing apparatus of the present invention, a Doppler shift signal is detected from a reception signal obtained by an ultrasonic transducer by transmitting/receiving an ultrasonic wave to/from an object to be diagnosed. Doppler data obtained from this detection signal is written in a memory and monochromatic ultrasonic image data obtained from the reception signal and the Doppler data read out from the memory are used to perform color processing of the ultrasonic image data in accordance with the detection signal, thereby displaying blood flow data. The ultrasonic diagnosing apparatus includes a mixing/processing section and a switching control section. The mixing/processing section includes a reversing section for reversing display colors associated with blood flow directions by performing complement processing of the Doppler data read out from the memory, and a selector section for selecting one of the Doppler data reversed by the reversing section and the non-reversed Doppler data read out from the memory. The mixing/processing section serves to mix the Doppler data selected by the selector section with the ultrasonic image data. The switching control section serves to arbitrarily control a selecting operation of the selector section in the mixing/processing section in accordance with an external operation.

In addition, an apparatus for displaying FFT (fast Fourier transform) Doppler data may include a processing section for reversing the display colors of the FFT Doppler data in synchronicity with reversal of the display colors of the blood flow directions.

According to the ultrasonic diagnosing apparatus of the present invention, the display colors of color Doppler display can be arbitrarily reversed with a simple operation. Even after freezing or in the process of cinematographic loop reproduction, an operator can reverse the display colors to set desired display colors with a simple operation without paying attention to blood flow directions. Therefore, the operation load of the operator can be reduced, and accurate ultrasonic diagnosis data can be obtained with a simple operation. In addition, the arrangement of the apparatus is not complicated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 5 is a block diagram showing a detailed arrangement of an ultrasonic diagnosing apparatus according to the second embodiment of the present invention;

DETAILED DESCRIPTION OF THE PREFERRED EMBODIMENT

Figure 1:
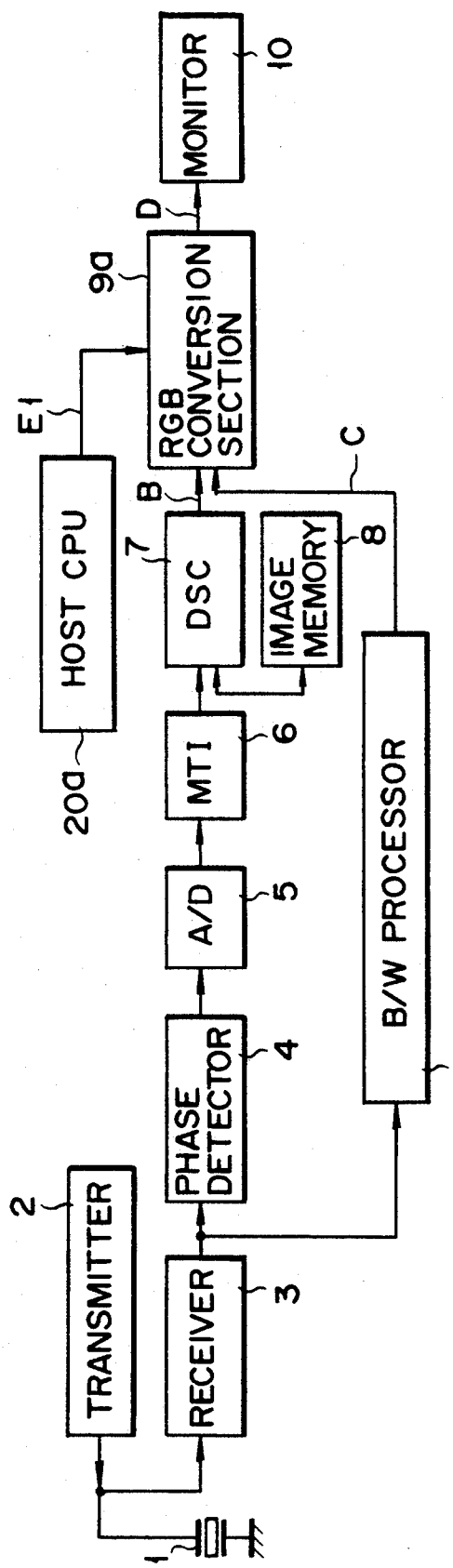
FIG. 1 is a block diagram showing a schematic arrangement of a conventional ultrasonic diagnosing apparatus.
Figure 2:
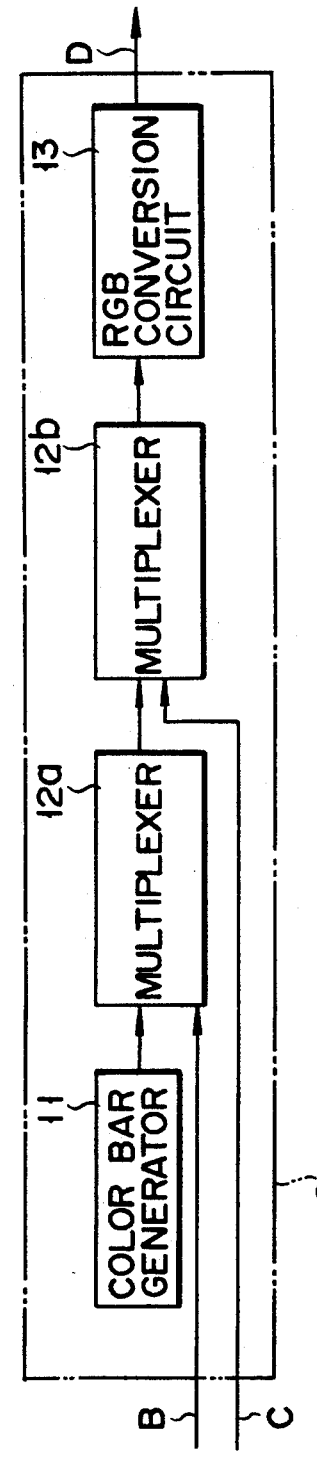
FIG. 2 is a block diagram showing a detailed arrangement of an RGB conversion section in the apparatus in FIG. 1.
Figure 3:
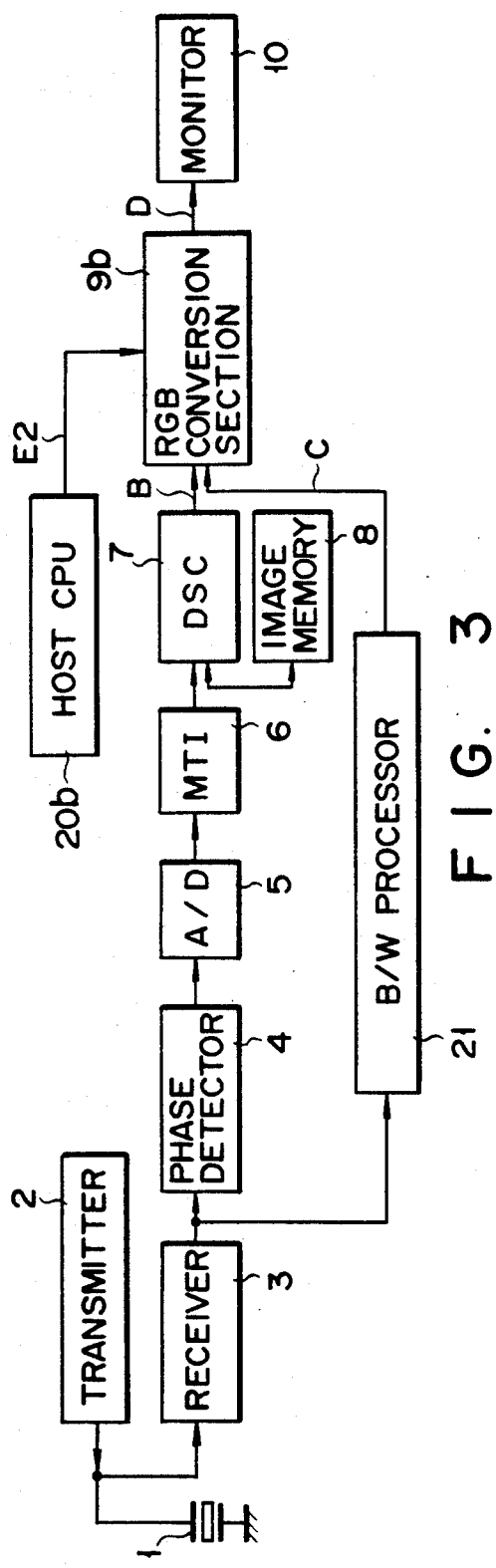
FIG. 3 is a block diagram showing a schematic arrangement of an ultrasonic diagnosing apparatus according to the first embodiment of the present invention.
Figure 4:
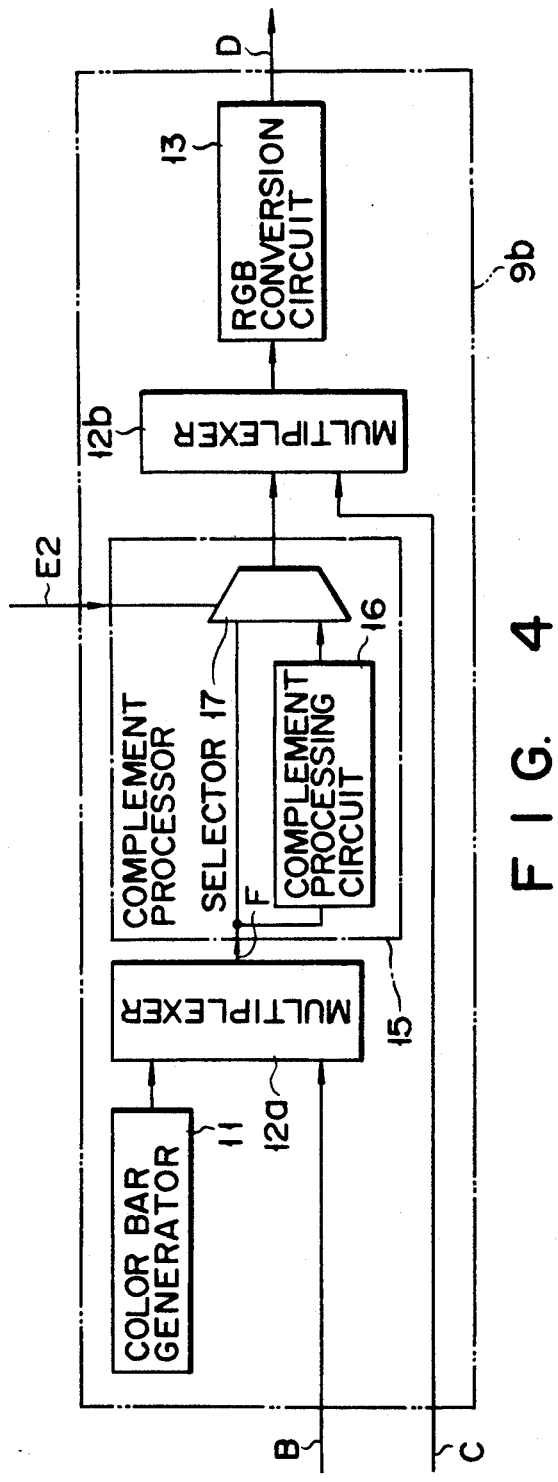
FIG. 4 is a block diagram showing a detailed arrangement of an RGB conversion section of the apparatus in FIG. 3.

FIG. 3 shows an arrangement of an ultrasonic diagnosing apparatus according to the first embodiment of the present invention. FIG. 4 shows a detailed arrangement of an RGB conversion section in the apparatus shown in FIG. 3. The same reference numerals in FIGS. 3 and 4 denote the same parts as in FIGS. 1 and 2.

An RGB conversion section 9b shown in FIG. 4 constitutes a principal characteristic feature of the apparatus of this embodiment. The RGB conversion section 9b includes a complement processor 15 having a complement processing circuit 16 and selector 17. A multiplexer 12a mixes Doppler data B output from a DSC 7, and color bar data output from a color bar generator 11. The Doppler data B includes blood flow velocity/direction data, turbulence data of blood flow velocity and Doppler power data. The complement processing circuit 16 then performs complement processing of the composite data to reverse display colors of the Doppler data B and the color bar data. The selector 17 receives output data from the complement processing circuit 16 and output data F from the multiplexer 12a and selectively supplies one of them to a multiplexer 12b. In addition, the apparatus of this embodiment includes a host CPU 20b for controlling a selecting operation of the selector 17 by supplying a control signal E2 to the complement processor 15.

The complement processor 15 includes, e.g., a ROM (read-only memory) for storing a complement conversion table, and can perform complement processing by using the complement conversion data table of the ROM. More specifically, input data to the complement processor 15 is numerical data to be converted into color data. By obtaining the complement of such numerical data, numerical data which is reverse to the input numerical data in terms of magnitude can be obtained. When such complement processing is to be performed by using a ROM, for example, complement data is stored at each address in the ROM so a to correspond to the value of its address data, and the complement data stored in the ROM is read out by using input data as address data. This readout data is then output as a conversion result. In addition, since the complement processor 15 is only required to perform an arithmetic operation for obtaining a complement, it may be constituted by a logic array, or a combination of generally used logic ICs (integrated circuits).

An operation of this apparatus will be described below.

An ultrasonic transducer 1 is driven by a transmitter 2. Ultrasonic pulses from the ultrasonic transducer 1 are repeatedly transmitted a predetermined number of times in the same beam direction. An ultrasonic wave is reflected by scattering substances such as blood cells in a living body and becomes a reflected ultrasonic wave, i.e., an ultrasonic echo. If the scattering substances are moving when the ultrasonic wave is reflected, the wave is subjected to a Doppler shift. Therefore, the reflected ultrasonic wave includes a Doppler shift data component based on the moving blood cells. This reflected ultrasonic wave is received by a receiver 3 through the ultrasonic transducer 1, and is detected by a phase detector 4, thus obtaining a reception signal consisting of a Doppler shift signal and an unnecessary clutter component. In addition, this reception signal is converted into a digital signal by an A/D converter 5, and the clutter component is removed by an MTI 6. The Doppler shift signal based on the blood flow is frequency-analyzed by a frequency analyzer in the MTI 6 so as to obtain Doppler data including turbulence data and Doppler signal power data. The Doppler data is then written in a frame memory in the DSC 7. An image memory 8 is used to store data of a plurality of frames, as needed, and to perform cinematographic loop reproduction for sequentially reading out these data and reproducing/displaying them.

Furthermore, the Doppler data including power, turbulence, velocity data, and the like, which is read out from the frame memory in the DSC 7, is input to the RGB conversion section 9b in synchronicity with a horizontal sync signal from a display system (H synchronization).

In the RGB conversion section 9b, the Doppler data B input from the DSC 7 to the RGB conversion section 9b is mixed with the color bar data from the color bar generator 11 by the multiplexer 12a.

A complement processing circuit 16 performs complement processing of an output signal F from the multiplexer 12a.

The control signal E2 from the host CPU 20b actuate the selector 17. The output signal F of the multiplexer 12a and a result of the complement processing of the complement processing circuit 16 are input to the selector 17 and the selector 17 selects the one of those two inputs corresponding to the control signal E2.

When an operator does not require a change in display color, e.g., display colors are proper with respect to blood flow directions (the forward direction is a direction approaching the ultrasonic transducer 1 and is an arterial blood flow direction indicated by red and the reverse direction is a direction moving away from the ultrasonic transducer and is a venous blood flow direction indicated by blue), since the control signal E2 from the host CPU 20b is not input to the complement processor 15, the selector 17 receives the composite data F (the Doppler data B and the color bar data) from the multiplexer 12a as it is. This composite signal is mixed with, e.g., black/white B mode data output from a B/W processor 21 by the multiplexer 12b, and is converted into color data by the RGB conversion circuit 13 so as to be output from a monitor 10 as a signal D.

Assume that the operator needs to change display colors. For example, when reverse display colors are set with respect to blood flow directions, i.e., a venous blood flow is indicated by red representing the forward direction and an arterial blood flow is indicated by blue representing the reverse direction, the operator turns on a forward/reverse direction switch arranged on an operation panel. This operation of the switch may be performed after freezing or in the process of cinematographic loop reproduction. As a result, the control signal E2 for commanding reversal of the display colors is input from the host CPU 20 to the complement processor 15. Upon reception of the control signal E2, the selector 17 selects the complement processing circuit 16 side. As a result, the composite data F (the Doppler data B and the color bar data) from the multiplexer 12a is subjected to complement processing in the complement processing circuit 16, and the display color data is reversed such that the forward direction is indicated by blue and the reverse direction is indicated by red. The signal whose display color data is reversed by the complement circuit 16 is supplied to the multiplexer 12b through the selector 17 and is mixed with the B mode data from the B/W processor 21 by the multiplexer 12b. The composite data is then color-converted by the RGB conversion circuit 13, and is output to the monitor 10 as the display signal D.

If color display data, such as color bar data, Doppler power data and blood velocity data, is reversed by the complement processor 15 in the RGB conversion section 9b, the operator can operate the apparatus without giving careful consideration to blood flow directions, and can reverse display colors to set desired display colors in a real-time manner while watching an image displayed as a result of the operation. The operator can concentrate on a scanning operation and the operation load can be reduced. In addition, since color displays can be easily reversed as needed, accurate ultrasonic diagnosis data can be easily obtained. Furthermore, display colors can be reversed even in the process of cinematographic loop reproduction using the image memory 8, and hence a two-dimensional Doppler tomographic image can be easily reproduced with display colors desired by the operator.

If the complement processor is arranged in the MTI, only a Doppler signal is reversed, and a complicated circuit is required to reverse color bar data. In this embodiment, however, since the complement processor is arranged between the multiplexers 12a and 12b in the RGB conversion section 9b, display colors can be arbitrarily reversed even after freezing, and only a simple circuit is required.

Figure 6:
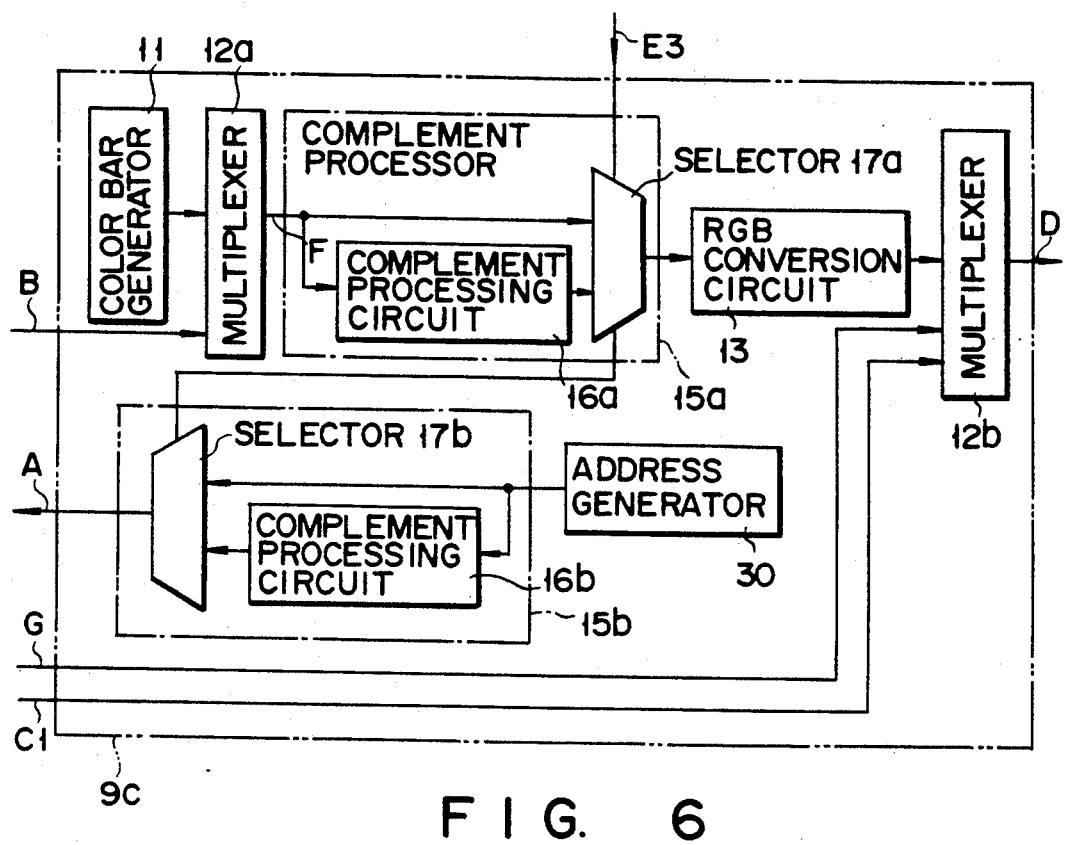
FIG. 6 is a block diagram showing a detailed arrangement of an RGB conversion section in the apparatus in FIG. 5.
Figure 7:
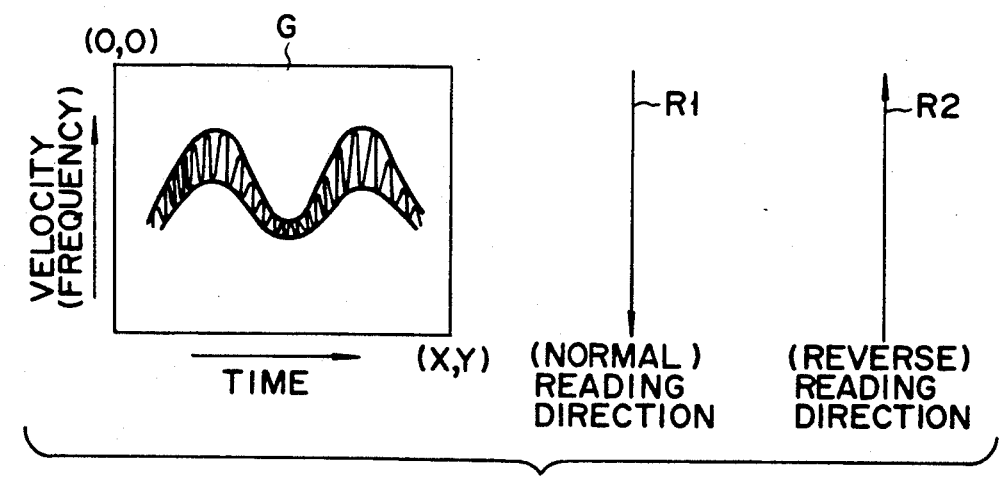
FIG. 7 is a view for explaining a forward/reverse display reversing function of an FFT Doppler system.

FIG. 5 shows an arrangement of an ultrasonic diagnosing apparatus according to the second embodiment. FIG. 6 shows an RGB conversion section in detail. FIG. 7 is a view for explaining a forward/reverse display reversing function of an FFT (fast Fourier transform) Doppler system in this embodiment.

In addition to the arrangement of the first embodiment, the second embodiment comprises an FFT processing system for displaying FFT Doppler data, which is constituted by an A/D converter 5b for converting phase-detected Doppler shift data into digital data, an FFT processor 25 for obtaining FFT Doppler data by performing an FFT operation of the Doppler shift data output from the A/D converter 5b, and a D/A (digital-to-analog) converter 26 for converting the FFT data obtained by the FFT processor 25 into analog data. A B/W processor 21 includes an envelope detector 22, an A/D converter 5c, a frame memory 7a, and an image memory 8a. An RGB conversion section 9c includes an address generator 30 and two complement processors 15a and 15b each having the same arrangement as that of the complement processor 15 in the first embodiment. Each of the frame and image memories 7a and 8a includes a pair of memories for respectively storing monochromatic B- or M-mode image data and FFT Doppler data.

The complement processor 15a reverses display color data consisting of color bar data and Doppler data B. The complement processor 15b reverses the forward-/reverse direction of blood flow velocity data of FFT Doppler data from the FFT system. Selectors 17a and 17b of these complement processors 15a and 15b are switched by a control signal E3 from the host CPU 20c in synchronicity with each other, and the forward-/reverse direction reversing functions of the display color data consisting of the color bar and the Doppler data B, and the FFT Doppler data are operated in synchronicity with the switching operation.

In the apparatus having the above-described arrangement, Doppler data obtained by a DSC 7 is input to the RGB conversion section 9c. In the FFT Doppler system, FFT Doppler data, which is obtained by processing a detection signal from a phase detector 4 in the FFT processor 25 through the A/D converter 5b, is written in the frame memory 7a through the D/A converter 26.

In the B/W processor system, a reception signal from a receiver 3 is input to the B/W processor 21 so as to be envelope-detected by the envelop detector 22, and is written in the frame memory 7a through the A/D converter 5c. FFT Doppler data G and B-mode data C1 are read out from the frame memory 7a and are input to the RGB conversion section 9c. In the RGB conversion section 9c, the following processing will be performed.

Assume that an operator needs to change display colors. For example, when reverse display colors are set with respect to blood flow directions, i.e., a venous blood flow is indicated by red representing the forward direction and a arterial blood flow is ndicated by blue representing the reverse direction, the operator turns on a forward/reverse direction reversing switch arranged on an operation panel. This operation of the switch may be performed after freezing or in the process of cinematographic loop reproduction. When the forward/reverse direction reversing switch is turned on, the control signal E3 for commanding reversal of display colors is input from the host CPU 20c to the complement processor 15a. The complement circuits 16a and 16b are respectively selected by the selectors 17a and 17b. The composite data F (the blood flow data B and the color bar data) from a multiplexer 12a is subjected to complement processing in the complement processing circuit 16a. As a result, the display color data is reversed so that the forward direction is indicted by blue, and the reverse direction is indicated by red. The signal whose display color data is reversed by the complement processing circuit 16a is subjected to color processing in an RGB conversion circuit 13, and is input to a multiplexer 12b.

FIG. 7 shows the FFT Doppler data G stored in the frame memory 7a. The forward/reverse direction reversing switch is normally turned off, and the data G is sequentially read out in a direction indicated by an arrow R1, and the image shown in FIG. 7 is displayed. When the forward/reverse direction reversing switch is turned on, the read direction in which the FFT Doppler data G is read out from the frame memory 7a is reversed. More specifically, since the complement processor 15b is reversed in synchronicity with the complement processor 15a by the control signal E3, the FFT Doppler data G is read out from the frame memory 7a in a direction indicated by an arrow R2 in FIG. 7. As a result, the FFT Doppler data G is reversed and is output to the multiplexer 12b as a reversed image.

The multiplexer 12b mixes the composite data of the blood flow data B and the color bar data which underwent color processing in the RGB conversion circuit 13, the FFT Doppler data G read out from the frame memory 7a and B-mode data C1 from the B/W processor 21, and supplies the resultant data to the monitor 10 as a display signal D.

As has been described above, according to this embodiment, since the complement processors 15a and 15b are operated in synchronicity with each other, FFT Doppler data can be reversed and displayed upon reversal of the display colors of Doppler data. With this operation, more effective display can be performed for clinical diagnosis or the like of a carotid artery.

The present invention is not limited to the above-described embodiments. Various changes and modifications can be made within the spirit and scope of the invention.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnosing apparatus comprising:
   ultrasonic wave transmitting/receiving means for transmitting and receiving an ultrasonic wave to and from an object, respectively;
   Doppler data extracting means for detecting a Doppler shift signal from a reception signal obtained by said ultrasonic wave transmitting/receiving means, and obtaining Doppler data from said detected Doppler shift signal;
   memory means for storing said Doppler data generated by said Doppler data extracting means;
   image generating means for obtaining ultrasonic image data from said reception signal obtained by said ultrasonic wave transmitting/receiving means;
   reversing means for performing complement processing of said Doppler data stored in said memory means, thereby reversing display colors associated with blood flow directions;
   selecting means for selecting one of said Doppler data reversed by said reversing means and said Doppler data stored in said memory means which has not been reversed by said reversing means;
   color processing means for obtaining according to said ultrasonic image data and one of said Doppler data selected by said selecting means; and
   display means for displaying said blood flow image data obtained by said color processing means.

2. An apparatus according to claim 1, wherein said Doppler data extracting means includes means for extracting blood flow velocity data as Doppler data.

3. An apparatus according to claim 1, wherein said image generating means includes means for obtaining B-mode image data as ultrasonic image data.

4. An apparatus according to claim 1, wherein said image generating means includes means for obtaining M-mode data as ultrasonic image data.

5. An apparatus according to claim 1, wherein said memory means comprises a frame memory for scan conversion.

6. An apparatus according to claim 1, wherein said reversing means comprises complement processing means for obtaining a complement of display color data.

7. An apparatus according to claim 1, further comprising color bar generating means for generating color bar data for displaying a color bar as a display color reference, said reversing means reversing display colors of said Doppler data and said color bar data, said selecting means selecting one of said Doppler data and said color bar data reversed by said reversing means and said Doppler data and said color bar data not reversed by said reversing means, and said color processing means obtaining blood flow image data according to said Doppler data and said color bar data.

8. An apparatus according to claim 1, wherein said reversing means includes means for obtaining numerical data which is opposite in magnitude to inputted numerical data, said inputted numerical data being said Doppler data.

9. An apparatus according to claim 1, wherein a Doppler shift caused by movement in a direction approaching an ultrasonic transducer is displayed in red when said non-reversed Doppler data is selected by said selecting means and a Doppler shift caused by movement in a direction approaching said ultrasonic transducer is displayed in blue when said reversed Doppler data is selected by said selecting means.

10. An ultrasonic diagnosing apparatus comprising:
ultrasonic wave transmitting/receiving means for transmitting and receiving an ultrasonic wave to and from an object, respectively;
Doppler data extracting means for detecting a Doppler shift signal from a reception signal obtained by said ultrasonic wave transmitting/receiving means, and obtaining Doppler data and FFT Doppler data from said detecting Doppler shift signal;
first memory means for storing said Doppler data generated by said Doppler data extracting means;
second memory means for storing said FFT Doppler data generated by said Doppler data extracting means;
image generating means for obtaining ultrasonic image data from said reception signal obtained by said ultrasonic wave transmitting/receiving means;
first reversing means for performing complement processing of said Doppler data stored in said first memory means, thereby reversing display colors associated with blood flow directions;
selecting means for selecting one of said Doppler data reversed by said first reversing means and said Doppler data stored in said memory means which has not been reversed by said reversing means;
second reversing means, operated in synchronicity with said selecting means, for reversing a said FFT Doppler data stored in said second memory means when said Doppler data reversed by said first reversing means is selected;
color processing means for obtaining blood flow image data according to ultrasonic image data and one of said Doppler data selected by said selecting means; and
display means for displaying said blood flow image data obtained by said color processing means and said FFT Doppler data read out from said second memory means.

11. An apparatus according to claim 10, wherein said Doppler data extracting means includes means for extracting blood flow velocity data as Doppler data.

12. An apparatus according to claim 10, wherein said image generating means includes means for obtaining B-mode image data as ultrasonic image data.

13. An apparatus according to claim 10, wherein said image generating means includes means for obtaining M-mode data as ultrasonic image data.

14. An apparatus according to claim 10, wherein said first memory means comprises a frame memory for scan conversion.

15. An apparatus according to claim 10, wherein said first reversing means comprises complement processing means for obtaining a complement of display color data.

16. An apparatus according to claim 10, further comprising color bar generating means for generating color bar data for displaying a color bar as a display color reference, said first reversing means reversing display colors of said Doppler data and said color bar data, said selecting means selecting one of said Doppler data and said color bar data reversed by said first reversing means and said Doppler data and said color bar data not reversed by said first reversing means, and said color processing means obtaining blow flow image according to said Doppler data and said color bar data.

17. An apparatus according to claim 10, wherein said reversing means includes means for obtaining numerical data which is opposite in magnitude to inputted numerical data, said inputted numerical data being said Doppler data and said FFT Doppler data.

18. An apparatus according to claim 10, wherein a Doppler shift caused by movement in a direction approaching an ultrasonic transducer is displayed in red when said non-reversed Doppler data is selected by said selecting means and a Doppler shift caused by movement in a direction approaching said ultrasonic transducer is displayed in blue when said reversed Doppler data is selected by said selecting means.

19. An ultrasonic diagnosing apparatus comprising:
ultrasonic wave transmitting/receiving means for transmitting and receiving an ultrasonic wave to and from an object;
Doppler data extracting means for detecting a Doppler shift signal from a reception signal obtained by said ultrasonic wave transmitting/receiving means, and obtaining Doppler data from said detected Doppler shift signal;
memory means for storing said Doppler data generated by said Doppler data extracting means;
reversing means for performing complement processing of said Doppler data stored in said memory means, thereby reversing display colors associated with blood flow directions;
selecting means for selecting one of said Doppler data reversed by said reversing means and said Doppler data stored in said memory means which has not been reversed by said reversing means;
color processing means, which uses one of said Doppler data selected by said selecting means, for obtaining color Doppler data by performing color processing of the Doppler data; and
display means for displaying said color Doppler data obtained by said color processing means.

20. An apparatus according to claim 19, wherein said reversing means includes means for obtaining numerical data which is opposite in magnitude to inputted numerical data, said inputted numerical data being said Doppler data.

21. An apparatus according to claim 19, wherein a Doppler shift caused by movement in a direction approaching an ultrasonic transducer is displayed in red when said non-reversed Doppler data is selected by said selecting means and a Doppler shift caused by movement in a direction approaching said ultrasonic transducer is displayed in blue when said reversed Doppler data is selected by said selecting means.

* * * * *